(12) United States Patent
Odawara

(10) Patent No.: US 8,026,075 B2
(45) Date of Patent: Sep. 27, 2011

(54) METHOD FOR STABILIZING COENZYME AND COMPOSITION THEREOF

(75) Inventor: Fumitomo Odawara, Shizuoka (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 12/977,874

(22) Filed: Dec. 23, 2010

(65) Prior Publication Data

US 2011/0159564 A1 Jun. 30, 2011

Related U.S. Application Data

(62) Division of application No. 11/576,048, filed as application No. PCT/JP2005/018424 on Oct. 5, 2005, now Pat. No. 7,879,567.

(30) Foreign Application Priority Data

Oct. 5, 2004 (JP) .................................. 2004-292710

(51) Int. Cl.
   *G01N 33/53* (2006.01)
   *G01N 31/00* (2006.01)

(52) U.S. Cl. ............ 435/7.21; 435/7.1; 436/1; 436/501; 436/518; 424/9.1; 424/520; 422/50; 530/300; 530/350

(58) Field of Classification Search .................. None
   See application file for complete search history.

(56) References Cited

U.S. PATENT DOCUMENTS

| 4,779,754 | A | 10/1988 | Ten Eyck et al. |
| 5,198,193 | A | 3/1993 | Bunce et al. |
| 5,354,538 | A | 10/1994 | Bunce et al. |
| 5,424,204 | A | 6/1995 | Aoyama et al. |
| 5,529,906 | A | 6/1996 | Shimizu et al. |
| 5,817,467 | A | 10/1998 | Aoyama et al. |
| 6,130,054 | A | 10/2000 | Iwata et al. |
| 6,811,753 | B2 | 11/2004 | Hirao et al. |
| 6,867,012 | B2 | 3/2005 | Kishimoto et al. |
| 7,501,053 | B2 | 3/2009 | Karinka et al. |
| 7,879,567 | B2 | 2/2011 | Odawara |
| 2001/0044128 | A1 | 11/2001 | Zielenski |
| 2002/0068349 | A1 | 6/2002 | Horinouchi et al. |
| 2004/0079653 | A1 | 4/2004 | Karinka et al. |
| 2005/0136505 | A1 | 6/2005 | Zielenski |

FOREIGN PATENT DOCUMENTS

| EP | 0821069 | 1/1998 |
| EP | 1083235 | 3/2001 |
| JP | 57-43684 | 3/1982 |
| JP | 62-151200 | 7/1987 |
| JP | 3-505261 | 11/1991 |
| JP | 6-153991 | 6/1994 |
| JP | 6-303996 | 11/1994 |
| JP | 10-33196 | 2/1998 |
| JP | 10-276785 | 10/1998 |
| JP | 11-253193 | 9/1999 |
| JP | 2001-61498 | 3/2001 |
| JP | 2001-238697 | 9/2001 |
| JP | 2005-304483 | 11/2005 |
| WO | 01/94370 | 12/2001 |

OTHER PUBLICATIONS

National Library of Medicine, "Disaccharides" <<www.nlm.nih.gov/cgi/mesh/2009/MB_cgi?mode=&term=Disaccharides>> Nov. 30, 2009.
Scientific Physic, "Carbohydrates—Chemical Structure" <<www.scientificpsychic.com/fitness/carbohydrates1.html>> Nov. 24, 2009.
"Stability and Storage of Frequently Used Co-Enzymes and Substrates", Basic Experimental Method for Protein and Enzyme, Nankodo Co., Ltd., pp. 422-428, 1994.
English language Abstract of WO 01/094370, Dec. 13, 2001.
English language Abstract of JP 57-43684, Mar. 11, 1982.
English language Abstract of JP 10-276785, Oct. 20, 1998.
English language Abstract of JP 2005-304483, Nov. 4, 2005.
English language Abstract of JP 2001-61498, Mar. 23, 2001.
English language Abstract of JP 6-303996, Nov. 1, 1994.
English language Abstract of JP 11-253193, Sep. 21, 1999.
English language Abstract of JP 62-151200, Jul. 6, 1987.
English language Abstract of JP 6-153991, Jun. 3, 1994.

*Primary Examiner* — Lisa Cook
(74) *Attorney, Agent, or Firm* — Greenblum & Bernstein, PLC

(57) ABSTRACT

Disclosed is a sugar and/or a sugar alcohol as a substance for suppressing dephosphorylation reaction of a phosphorylated coenzyme. Also disclosed is a method for stabilizing a phosphorylated coenzyme which is characterized by having at least a substance for suppressing dephosphorylation reaction of the phosphorylated coenzyme coexist with the phosphorylated coenzyme.

11 Claims, 1 Drawing Sheet

METHOD FOR STABILIZING COENZYME AND COMPOSITION THEREOF

CROSS-REFERENCE TO RELATED APPLICATION

This application is a divisional of U.S. application Ser. No. 11/576,048, which is a national stage of International Application PCT/JP2005/018424, filed Oct. 5, 2005, which claims priority to Japanese Application No. 2004-292710, filed Oct. 5, 2004. The disclosures of application Ser. No. 11/576,048 and PCT/JP2005/018424 are incorporated by reference herein in their entireties.

TECHNICAL FIELD

The present invention relates to a stabilization method for a phosphorylated coenzyme characterized by allowing at least a substance for suppressing dephosphorylation reaction of the phosphorylated coenzyme to coexist with the phosphorylated coenzyme, a preservation method therefor, or a stabilized composition. The present invention is used in the field of clinical diagnosis, food evaluation, and an assay for biogenic substances.

BACKGROUND ART

Heretofore, coenzymes have been frequently used for chemical reagents for biochemical clinical investigations. Coenzymes, which have been used, include oxidation or reduction type nicotinamide adenine dinucleotide (NADH or NAD) or nicotinamide adenine dinucleotide phosphate (NADPH or NADP). However, those coenzymes have a problem with stability. The coenzyme changes to an oxidized coenzyme, NAD or NADP, by a very small amount of an enzyme included in an assay reagent, or disintegrates ADP ribose and others, thereby resulting in a change in structure which can be used by an enzyme. Therefore, there is a problem in that such a change leads to a decrease in total amount of the coenzyme and then lowers the sensitivity of the assay agent (Non-patent Document 1). For solving this problem, it is known that a coenzyme is preserved under temperature conditions as low as possible, such as under freezer storage or cold storage and a coenzyme-containing reagent is then freeze-dried. Alternatively, it is known that, as stabilizers for preserving the coenzyme in a state of solution, there are used, for example, an amine base, sodium hydroxide, a chelating agent, azide, boric acid, an alkali metal, an ammonium bicarbonate buffer, and an active-oxygen removing substance. Any of these methods has been conceived with the intention of preventing the coenzyme from being decomposed as described above to avoid a decrease in sensitivity (Patent Document 1 and Patent Document 2).

Coenzymes are used for immunologic clinical diagnostic reagents. For instance, in an enzymatic immunoassay, there has been known a coenzyme-cycling method as a method of detecting an alkaline-phosphatase (ALP)-labeled antibody with a phosphorylated coenzyme, NADP or NADPH, which is used as a substrate (Patent Document 3). Detection methods using enzyme-cycling reagents made of NADP or NADPH, alcohol dehydrogenase, diaphorase, alcohol, and tetrazolium salt have been well known in the art. For example, when NADP is used as a substrate for ALP, NAD is produced from NADP by ALP and the resulting NAD is then converted into NADP by alcohol dehydrogenase and alcohol. Subsequently, NADH returns to NAD by diaphorase and tetrazolium salt and the reaction of converting NAD to NADH then proceeds again. In this way, through the cyclic reaction between NAD and NADH, formazan dyes produced from tetrazolium salt accumulate in a reaction solution. Thus, the amount of the dyes is measured to determine the activity of ALP.

Even those reagents also have problems with stability of coenzyme, like biochemical reagents, for prolonged preservation of the reagents, coenzymes have been preserved in a free-dried state under temperature conditions as low as possible, such as under freezer storage or cold storage. In addition, an attempt has been made by selecting an appropriate buffer for stabilization.

In contrast, in recent years, simple assays, which are typified by assay reagents for influenza antigen and capable of obtaining assay results on the spot in a medical office or at bedside, have been becoming popular. Any of these point-of-care (POC) test reagents requires, if it should be preserved under cold storage or preservation of lower temperature, a specific device, such as a refrigerator or a freezer, and the preservation space for the reagent is also limited, so there is a problem in that a large amount of the reagent cannot be purchased and preserved. Therefore, a reagent, which can be preserved at room temperature, has been demanded. However, in these POC test reagents, for providing a reagent using a coenzyme for practical use, which can be preserved at room temperature, a prolonged preservation stability under severe conditions than the conventional refrigerating preservation has been already difficult as described above and now such a preservation stability should be attained under more severe conditions. Therefore, the practical use of a test reagent using a coenzyme in this field has been extremely difficult.

In addition, in the field of test reagents, in order to measure a very small amount of a substance of interest, it is demanded to enhance the sensitivity of the measurement. ALP has been well known as a target enzyme generally used in an enzymatic immunoassay, so a procedure of detecting ALP at high sensitivity has been demanded. In addition, the technique of enhancing the sensitivity is useful not only for microassay but also for reduction in amount of a sample or shortening the measuring time. Thus, this is the most desired technique in this field.

[Patent Document 1] JP 3470099 B
[Patent Document 2] JP 2001-61498 A
[Patent Document 3] JP 06-303996 A
[Non-patent Document 1] Basic experimental method for protein and enzyme, Nankodo Co., Ltd., page 426

DISCLOSURE OF THE INVENTION

Problem to be Solved by the Invention

It is an object of the present invention to provide a stabilization method for a phosphorylated coenzyme for a prolonged period particularly at room temperature.

Means for Solving the Problem

The inventors of the present invention have concentrated on intensive study in consideration of the following viewpoints in particular to solve the above-mentioned problems. As a result, the inventors of the present invention have finally completed the present invention by finding out a stabilization method for a coenzyme, by which the coenzyme can be stably preserved at room temperature for a prolonged time. In an assay for ALP activity using a coenzyme, it is very difficult to attain the practical use of a reagent that allows the assay to be stably performed with good reproducibility for a prolonged time. Besides, in particular, for the practical use of a reagent for ALP activity assay with the use of a high-sensitive coenzyme-cycling method, which can be preserved at room temperature for a prolonged time, there is a need of the technique of coenzyme stabilization, which is capable of lowering non-specific color development which increases in proportion to an increase in preservation period. Thus, the inventors of the present invention have studied in consideration of limitations in known stabilization techniques and an importance in finding of a novel stabilization method.

That is, the present invention relates to a stabilization method for a phosphorylated coenzyme, characterized by allowing at least a substance for suppressing dephosphorylation reaction of the phosphorylated coenzyme to coexist with the phosphorylated coenzyme, and relates to:

(1) a stabilization method for a phosphorylated coenzyme, comprising allowing at least a substance for suppressing dephosphorylation reaction of a phosphorylated coenzyme to coexist with a phosphorylated coenzyme (2) a stabilization method for a phosphorylated coenzyme in a dry state, comprising: allowing at least a substance for suppressing dephosphorylation reaction of a phosphorylated coenzyme to coexist with a phosphorylated coenzyme in a solution; and drying the solution;

(3) the stabilization method according to the above-mentioned item (1) or (2), wherein the substance for suppressing dephosphorylation reaction is a sugar and/or a sugar alcohol;

(4) the stabilization method according to the above-mentioned item (1) or (2), wherein the substance for suppressing dephosphorylation reaction is a polysaccharide containing glucose as a constituent;

(5) the stabilization method according to the above-mentioned item (4), wherein the substance for suppressing dephosphorylation reaction is a disaccharide containing glucose as a constituent;

(6) the stabilization method according to the above-mentioned item (5), wherein the substance for suppressing dephosphorylation reaction is one or a combination of two or more selected from the group consisting of lactose, trehalose, maltose, and sucrose;

(7) the stabilization method according to the above-mentioned item (2), wherein the drying is performed by air drying;

(8) the stabilization method according to any one of the above-mentioned items (1) to (7), wherein the phosphorylated coenzyme is nicotinamide adenine dinucleotide phosphate (NADP);

(9) a stabilized composition of a phosphorylated coenzyme, comprising: at least a substance for suppressing dephosphorylation reaction of a phosphorylated coenzyme and a phosphorylated coenzyme;

(10) a stabilized composition of a phosphorylated coenzyme in a dry state, comprising at least a substance for suppressing dephosphorylation reaction of the phosphorylated coenzyme and a phosphorylated coenzyme;

(11) the stabilized composition according to the above-mentioned item (9) or (10), wherein the substance for suppressing dephosphorylation reaction is a sugar and/or a sugar alcohol;

(12) the stabilized composition according to the above-mentioned item (9) or (10), wherein the substance for suppressing dephosphorylation reaction is a polysaccharide containing glucose as a constituent;

(13) the stabilized composition according to the above-mentioned item (12), wherein the substance for suppressing dephosphorylation reaction is a disaccharide containing glucose as a constituent;

(14) the stabilized composition according to the above-mentioned item (13), wherein the substance for suppressing dephosphorylation reaction is one or a combination of two or more selected from the group consisting of lactose, trehalose, maltose, and sucrose;

(15) the stabilized composition according to any one of the above-mentioned items (9) to (14), wherein the phosphorylated coenzyme is nicotinamide adenine dinucleotide phosphate (NADP);

(16) a use of a substance for suppressing dephosphorylation reaction for stabilizing a phosphorylated coenzyme for a prolonged period;

(17) a use of a polysaccharide containing glucose as a constituent for preventing at least a phosphorylated coenzyme from dephosphorylation reaction;

(18) a preservation method for a phosphorylated coenzyme for a prolonged period, wherein the preservation method utilizes at least a substance for suppressing dephosphorylation reaction of the phosphorylated coenzyme;

(19) a stabilization method for a phosphorylated coenzyme for enzyme-cycling, comprising allowing a phosphorylated coenzyme to coexist with at least a substance for suppressing dephosphorylation reaction of the phosphorylated coenzyme;

(20) a stabilization method for a phosphorylated coenzyme for enzyme-cycling, comprising allowing only a phosphorylated coenzyme to coexist with at least a substance for suppressing dephosphorylation reaction of the phosphorylated coenzyme;

(21) the stabilization method according to the above-mentioned item (19) or (20), wherein the stabilization method for a phosphorylated coenzyme for enzyme-cycling is a stabilization method in which 70% or more of the phosphorylated coenzyme remains after preserving at 32° C. for three months and a ratio of a dephosphorylated coenzyme in the remaining phosphorylated coenzyme is less than 1%;

(22) the stabilization method according to the above-mentioned item (19) or (20), wherein the stabilization method for a phosphorylated coenzyme for enzyme-cycling is a stabilization method in which 70% or more of the phosphorylated coenzyme remains after preserving at 32° C. for six months and a ratio of a dephosphorylated coenzyme in the remaining phosphorylated coenzyme is less than 1%;

(23) the stabilization method according to the above-mentioned item (19) or (20), wherein the stabilization method for a phosphorylated coenzyme for enzyme-cycling is a stabilization method in which 70% or more of the phosphorylated coenzyme remains after preserving at 32° C. for one year and a ratio of a dephosphorylated coenzyme in the remaining phosphorylated coenzyme is less than 1%;

(24) the stabilization method according to any one of the above-mentioned items (19) to (23), wherein the phosphorylated coenzyme includes nicotinamide adenine dinucleotide phosphates;

(25) the stabilization method according to the above-mentioned item (24), wherein the nicotinamide adenine dinucleotide phosphates are nicotinamide adenine dinucleotide phosphate and/or thionicotinamide adenine dinucleotide phosphate;

(26) the stabilization method according to the above-mentioned item (25), wherein the nicotinamide adenine dinucleotide phosphate and/or thionicotinamide adenine dinucleotide phosphate include/includes nicotinamide adenine dinucleotide phosphate;

(27) the stabilization method according to the above-mentioned item (25), wherein the nicotinamide adenine dinucleotide phosphate and/or thionicotinamide adenine dinucleotide phosphate include/includes thionicotinamide adenine dinucleotide phosphate;

(28) the stabilization method according to any one of the above-mentioned items (19) to (27), wherein at least the substance for suppressing dephosphorylation reaction of the phosphorylated coenzyme is a polysaccharide that contains glucose as a constituent;

(29) the stabilization method according to the above-mentioned item (28), wherein the polysaccharide that contains glucose as a constituent is a disaccharide that contains glucose as a constituent;

(30) the stabilization method according to the above-mentioned item (29), wherein the disaccharide that contains glucose as a constituent is one or a combination of two or more selected from the group consisting of maltose, sucrose, lactose, and trehalose;

(31) the stabilization method according to the above-mentioned item (30), wherein the disaccharide that contains glucose as a constituent is one or a combination of two or more selected from the group consisting of maltose, trehalose, and lactose;

(32) the stabilization method according to the above-mentioned item (30), wherein the disaccharide that contains glucose as a constituent is maltose and/or lactose;

(33) the stabilization method according to the above-mentioned item (30), wherein the disaccharide that contains glucose as a constituent is lactose and/or trehalose;

(34) the stabilization method according to the above-mentioned item (30), wherein the disaccharide that contains glucose as a constituent is maltose and/or trehalose;

(35) the stabilization method according to the above-mentioned item (30), wherein the disaccharide that contains glucose as a constituent is lactose and/or sucrose;

(36) the stabilization method according to the above-mentioned item (30), wherein the disaccharide that contains glucose as a constituent is maltose and/or sucrose;

(37) the stabilization method according to the above-mentioned item (30), wherein the disaccharide that contains glucose as a constituent is lactose;

(38) the stabilization method according to the above-mentioned item (30), wherein the disaccharide that contains glucose as a constituent is maltose;

(39) the stabilization method according to the above-mentioned item (30), wherein the disaccharide that contains glucose as a constituent is sucrose;

(40) the stabilization method according to the above-mentioned item (30), wherein the disaccharide that contains glucose as a constituent is trehalose;

(41) the method of measuring the activity of alkaline phosphatase, wherein the stabilized composition according to any one of the above-mentioned items (9) to (15) is used;

(42) a flow-through simplified immunoassay device, comprising a solution-sending device which allows addition of an enzyme substrate to be automatically performed after allowing an enzyme-labeled reagent to permeate through an antibody- or antigen-immobilized membrane;

(43) the simplified immunoassay device according to the above-mentioned item (42), wherein the solution-sending device uses a water-soluble filter;

(44) the simplified immunoassay device according to the above-mentioned item (42) or (43), wherein the solution-sending device uses a siphon;

(45) the simplified immunoassay device according to any one of the above-mentioned items (42) to (44), wherein the enzyme substrate is a solution containing the stabilized composition according to any one of the above-mentioned items (9) to (15);

(46) the simplified immunoassay device according to any one of the above-mentioned items (42) to (45), wherein the simplified immunoassay device prevents a washing solution from being added after allowing the enzyme-labeled reagent to permeate through the antibody- or antigen-immobilized membrane and before automatically adding the enzyme substrate;

(47) an enzymatic immunoassay using the method of measuring the activity of alkaline phosphatase according to the above-mentioned item (41), wherein an antibody against a microbial ribosomal protein is used;

(48) the enzymatic immunoassay according to the above-mentioned item (47), wherein the microorganism is one or more selected from *Mycoplasma pneumoniae, Hemophilus influenza, Streptococcus pneumoniae, Chlamydia pneumoniae, Chlamydia trachomatis*, and *Legionella pneumophila;*

(49) the enzymatic immunoassay according to the above-mentioned item (47) or (48), wherein the ribosomal protein is 1.7/L12;

(50) the simplified immunoassay device according to any one of the above-mentioned items (42) to (46), wherein an antibody against the ribosomal protein of the microorganism is used;

(51) the simplified immunoassay device according to the above-mentioned item (50) using the enzymatic immunoassay according to the above-mentioned item (48), wherein the microorganism is one or more selected from the group consisting of *Mycoplasma pneumoniae, Hemophilus influenza, Streptococcus pneumoniae, Chlamydia pneumoniae, Chlamydia trachomatis*, and *Legionella pneumophila* is used;

(52) the enzymatic immunoassay according to the above-mentioned item (50) or (51), using the enzymatic immunoassay according to the above-mentioned item (49), wherein the ribosomal protein is L7/L12;

(53) the stabilization method according to any one of the above-mentioned items (1) to (8), further comprising allowing a citrate to coexist;

(54) the stabilization method according to the above-mentioned item (53), wherein the citrate is sodium citrate;

(55) the stabilized composition according to any one of the above-mentioned items (9) to (15), further comprising allowing a citrate to coexist;

(56) the stabilized composition according to the above-mentioned item (55), wherein the citrate is sodium citrate;

(57) the use according to the above-mentioned item (16) or (17), wherein a citrate is used;

(58) the use according to the above-mentioned item (57), wherein the citrate is sodium citrate;

(59) the preservation method for phosphorylated coenzyme for a prolonged period according to the above-mentioned item (18), wherein a citrate is used;

(60) the stabilization method according to any one of the above-mentioned items (19) to (40), wherein a citrate is further used;

(61) the stabilization method according to the above-mentioned item (60), wherein the citrate is sodium citrate;

(62) a method of measuring the activity of alkaline phosphatase, wherein the stabilized composition according to any one of the above-mentioned items (55) to (56) is used;

(63) the simplified immunoassay device as described in any one of the above-mentioned items (42) to (44), wherein the enzyme substrate is a solution containing the stabilized composition according to the above-mentioned item (55) or (56);

(64) the simplified immunoassay device according to the above-mentioned item (63), wherein a washing solution is not added after allowing the enzyme-labeled reagent to permeate through the antibody- or antigen-immobilized membrane and before automatically adding the enzyme substrate;

(65) an enzymatic immunoassay using the method of measuring the activity of alkaline phosphatase according to the above-mentioned item (62), wherein an antibody against a microbial ribosomal protein is used;

(66) the enzymatic immunoassay according to the above-mentioned item (65), wherein the microorganisms is one or more selected from the group consisting of *Mycoplasma pneumoniae, Hemophilus influenza, Streptococcus pneumoniae, Chlamydia pneumoniae, Chlamydia trachomatis*, and *Legionella pneumophila;*

(67) the enzymatic immunoassay according to the above-mentioned item (66) or (67), wherein the ribosomal protein is L7/L12;

(68) the simplified immunoassay device according to the above-mentioned item (63) or (64), wherein an antibody against the ribosomal protein of the microorganism is used;

(69) the simplified immunoassay device according to the above-mentioned item (68), wherein the microorganism is one or more selected from the group consisting of *Mycoplasma pneumoniae, Hemophilus influenza, Streptococcus pneumoniae, Chlamydia pneumoniae, Chlamydia trachomatis*, and *Legionella pneumophila* is used;

(70) the enzymatic immunoassay according to the above-mentioned item (50) or (51), wherein the ribosomal protein is L7/L12;

(71) the stabilization method according to the above-mentioned item (1), wherein at least a substance for suppressing dephosphorylation reaction of the phosphorylated coenzyme coexists only with a phosphorylated coenzyme;

(72) the stabilization method according to the above-mentioned item (2), wherein at least a substance for suppressing dephosphorylation reaction of the phosphorylated coenzyme coexists only with a phosphorylated coenzyme;

(73) the stabilization method according to the above-mentioned item (71) or (72), wherein the substance for suppressing dephosphorylation reaction is a sugar and/or a sugar alcohol;

(74) the stabilization method according to the above-mentioned item (71) or (72), wherein the substance for suppressing dephosphorylation reaction is a polysaccharide containing glucose as a constituent;

(75) the stabilization method according to the above-mentioned item (74), wherein the substance for suppressing dephosphorylation reaction is a disaccharide containing glucose as a constituent;

(76) the stabilization method according to the above-mentioned item (75), wherein the substance for suppressing dephosphorylation reaction is one or a combination of two or more selected from the group consisting of lactose, trehalose, maltose, and sucrose;

(77) the stabilization method according to the above-mentioned item (72), wherein the drying is performed by air drying;

(78) the stabilization method according to any one of items (71) to (77), wherein the phosphorylated coenzyme is nicotinamide adenine dinucleotide phosphate (NADP);

(79) the stabilized composition according to the above-mentioned item (9), comprising only at least a substance for suppressing dephosphorylation reaction of a phosphorylated coenzyme and a phosphorylated coenzyme;

(80) the stabilized composition according to the above-mentioned item (10), comprising only at least a substance for suppressing dephosphorylation reaction of a phosphorylated coenzyme and a phosphorylated coenzyme;

(81) the stabilized composition according to the above-mentioned item (79) or (80), wherein the substance for suppressing dephosphorylation reaction is a sugar and/or a sugar alcohol;

(82) the stabilized composition according to the above-mentioned item (79) or (80), wherein the substance for suppressing dephosphorylation reaction is a polysaccharide containing glucose as a constituent;

(83) the stabilized composition according to the above-mentioned item (82), wherein the substance for suppressing dephosphorylation reaction is a disaccharide containing glucose as a constituent;

(84) the stabilized composition according to the above-mentioned item (83), wherein the substance for suppressing dephosphorylation reaction is one or a combination of two or more selected from the group consisting of lactose, trehalose, maltose, and sucrose;

(85) the stabilized composition according to any one of the above-mentioned items (79) to (84), wherein the phosphorylated coenzyme is nicotinamide adenine dinucleotide phosphate (NADP);

(86) a method of measuring the activity of alkaline phosphatase, wherein the stabilized composition according to any one of the above-mentioned items (79) to (85) is used;

(87) the simplified immunoassay device as described in any one of the above-mentioned items (42) to (44), wherein the enzyme substrate is a solution containing the stabilized composition according to any one of the above-mentioned items (79) to (85);

(88) the stabilization method according to any one of the above-mentioned items (71) to (78), further including allowing a citrate to coexist;

(89) the stabilization method according to the above-mentioned item (88), wherein the citrate is sodium citrate;

(90) the stabilized composition according to any one of the above items (79) to (85), wherein a citrate further coexist;

(91) the stabilized composition according to the above-mentioned item (90), wherein the citrate is sodium citrate;

(92) a use of a substance for suppressing dephosphorylation reaction for stabilizing a phosphorylated coenzyme for a prolonged period;

(93) a use of only a polysaccharide containing glucose as a constituent and citric acid for preventing at least a phosphorylated coenzyme from dephosphorylation reaction;

(94) the use according to the above-mentioned item (92) or (93), wherein the citrate is sodium citrate;

(95) a preservation method for phosphorylated coenzyme for a prolonged period, wherein at least a substance for suppressing dephosphorylation reaction of the phosphorylated coenzyme is used; and

(96) a preservation method for phosphorylated coenzyme for a prolonged period, wherein only at least a substance for suppressing dephosphorylation reaction of the phosphorylated coenzyme and a citrate are used.

Effects of the Invention

The stabilization method of the present invention exhibits an effect of stabilizing a coenzyme at room temperature for a prolonged period, for example, when the stabilization method is used for measuring the activity of ALP, or the like. Therefore, it is very useful for achieving the practical use of a test reagent using a coenzyme in a POC test reagent or the like.

BEST MODE FOR CARRYING OUT THE INVENTION

Figure 1:
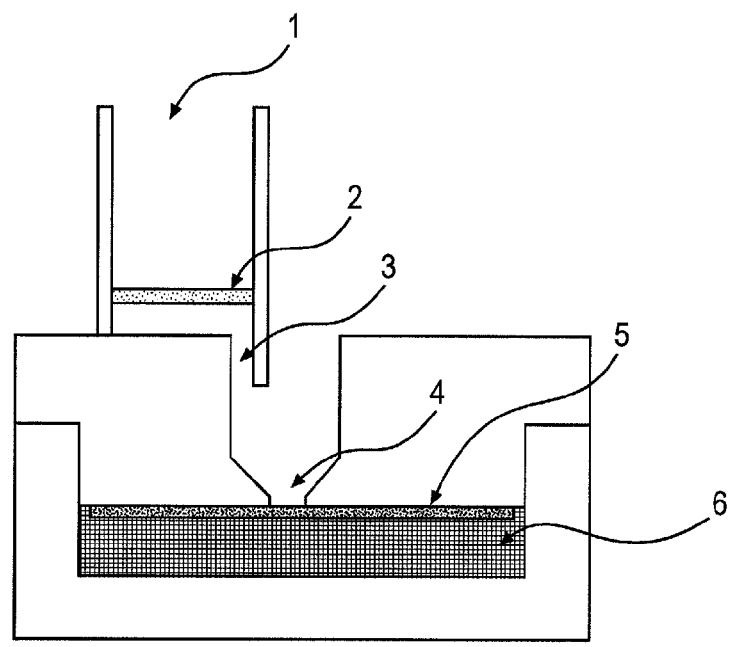
FIG. 1 is a drawing showing a flow-through-type simplified immunoassay device of the present invention, which is provided with a solution-sending device so that an enzyme substrate is automatically added after allowing an enzyme-labeled reagent to permeate through an antibody- or antigen-immobilized membrane.

Hereinafter, the present invention will be described in detail.

A preferable example of the phosphorylated coenzyme of the present invention is one or a combination of two or more coenzymes selected from the group consisting of NADP, thio-NADP, acetyl-NADP, deamino-NADP, and deamide-NADP. NADP or NADPH is more preferable, and NADP is particularly preferable. The purity of the coenzyme is higher the better. Any commercial product may be used without modification if it is of high purity. If necessary, commercial coenzyme powder dissolved in a suitable solvent and purified by column purification or the like may be used. Impurities, which must be taken into consideration, include unphosphorylated coenzymes and the like. The amount of the unphosphorylated coenzyme, that is, the impurities, is preferably 1% or less, more preferably 0.5% or less, particularly preferable 0.1% or less with respect to the amount of the phosphorylated coenzyme provided as a target of the stabilization in the present invention.

Substances that inhibit the dephosphorylation reaction in the present invention are not particularly limited as far as they have effects to prevent a phosphoric group bound to position 2 of ribose present in at least the structure of the above phosphorylated coenzyme from dissociating therefrom. In addition to such effects, the substances may have other effects. The other effects include those for preventing degradation of the binding between a ribose portion and a base portion. Specific examples of the substances include preferably sugars and/or sugar alcohols, particularly preferably sugars.

As the sugars, polysaccharides are preferable. For example, polysaccharides containing glucose in their structures are particularly preferable. Specific examples of the polysaccharides include sucrose, trehalose, lactose, maltose, α-cyclodextrin, β-cyclodextrin, γ-cyclodextrin, methyl-γ-cyclodextrin, hydroxypropylcyclodextrin, maltodextrin, maltotriose, maltotetraose, maltopentaose, maltohexaose, maltoheptaose, isomaltose, isomaltotriose, isomaltotetraose, isomaltopentaose, isomaltohexaose, panose, isopanose, sophorose, sophorotriose, sophorotetraose, sophoropentaose, sophorohexaose, kojibiose, laminaribiose, laminaritriose, laminaritetraose, laminaripentaose, nigerose, nigerotriose, cellobiose, cellotiose, cellotetraose, cellopentaose, cellohexaose, celloheptaose, gentiobiose, gentiobiose, gentiotetraose, gentiopentaose, gentiohexaose, neotrehalose, isotrehalose, vicianose, isoprimeverose, sambubiose, primeverose, lycotetraose, solabiose, melibiose, manninotriose, verbascotetraose, lycobiose, lycotriose, epiceilobiose, turanose, maltulose, isokestose, erlose, kestose, planteose, planteotetraose, raffinose, stachyose, verbascose, ajugose, lychnose, scillabiose, neohesperidose, rutinose, chacotriose, solatriose, fucosidolactose, difucolactose, strophantobiose, strophantotriose, digyranidobiose, digyranidotriose, odorotriose, trehalosamine, lacto-N-triose II, gentianose, neokestose, melezitose, neobifurcose, nystose, bifurcose, lycoricine, epigentiobiose, isolychnase, umbelliferose, sesamose, lacto-N-tetraose, lacto-N-neotetraose, cellobio uronic acid, N-acetylneuraminolactose I, N-acetylneuraminolactose II, di-N-acetylneuraminolactose, lactopentasaccharide a, lactopentasaccharide b, lactopentasaccharide c, glucosylmannitol, diglucosylmannitol, galactofuranosyl-glucosyl-galactofuranosyl-galactosyl-ribitol, amylose, glycogen, glucan, scierotan, dextran, nigeran, pstulan, pullulan, laminaran, rinaken, inulin, and a polysaccharide antigen on a surface of a bacterium.

Disaccharides that contain glucose in their structures are further preferable. Optimally, one or a combination of two or more selected from the group consisting of lactose, trehalose, maltose, and sucrose is preferable. In particular, lactose is preferable. Furthermore, in another aspect, trehalose may be preferable. In still another aspect, maltose may be preferable. In an alternate aspect, sucrose may be preferable. A preferable combination is of lactose or trehalose with any of other disaccharides containing glucose in their structures, for example, it is preferable to add to lactose a saccharide of one or a combination of two or more selected from trehalose, maltose, and sucrose or add to trehalose a saccharide of one or a combination of two or more selected from lactose, maltose, and sucrose. The ratio for the combination is not particularly limited as far as a desired effect is exerted. In view of convenience, however, one is defined as 1 and the other is defined as preferably an integral multiplication selected from 1 to 100, more preferably an integral multiplication selected from 1 to 10, further preferably an integral multiplication selected from 1 to 5, particularly preferably an integral multiplication selected from 1 to 3, extremely preferably 1 or 2 times, most preferably 1 time (=equal amount) in weight, volume, or mole.

The concentration range of the substance that inhibits the dephosphorylation reaction during preservation is not particularly limited, and the upper limit thereof may be any of concentrations as far as it is equal to or less than a saturated solubility concentration thereof. In contrast, the lower limit is preferably 0.1% or more, more preferably 0.5% or more, particularly preferably 1% or more.

The stabilization of the phosphorylated coenzyme in the present invention means the state of retaining the high purity of the phosphorylated coenzyme during its preservation period. Specifically, it means that the phosphorylated coenzyme is retained at high purity so that the content thereof is sufficient to be provided as an alkaline phosphatase substrate and an increase in background can be held down during the preservation period. More specifically, for example, the state in which the amount of the phosphorylated coenzyme may be 70% or more and the rate of an increase in unphosphorylated coenzyme to the amount of the phosphorylated coenzyme at the initial stage of the preservation may be kept at 1% or less for a prolonged period. More preferably, the state in which the amount of the phosphorylated coenzyme may be 80% or more and the rate of an increase in unphosphorylated coenzyme to the amount of the phosphorylated coenzyme at the initial stage of the preservation may be kept at 1% or less for a prolonged period. The preferable prolonged period may be three, six, or twelve months or more, and among them, 6 months or more is a particularly preferable period.

The stabilization method for a phosphorylated coenzyme of the present invention has a characteristic feature in that at least a phosphorylated coenzyme and a substance for suppressing dephosphorylation reaction are allowed to coexist with each other. The ratio of the phosphorylated coenzyme to the substance for suppressing dephosphorylation reaction in coexistence is not particularly limited as far as the phosphorylated coenzyme is sufficiently stabilized under the desired preservation conditions and the function of the phosphorylated coenzyme is not inhibited under the desired sample-measurement conditions. For instance, a preferable ratio is from $10^7$ molecules to 0.001 molecules, preferably from $10^6$ molecules to 0.001 molecules, optimally $10^6$ molecules to 0.002 molecules of the substance for suppressing dephosphorylation reaction to one molecule of the phosphorylated coenzyme.

Furthermore, a stabilization method using an appropriate buffer as an additive can be mentioned. The buffer may be added with an appropriate concentration of the phosphorylated coenzyme. The concentration range of the phosphorylated coenzyme is not particularly limited, but the lower limit thereof is preferably 0.1 mM or more, more preferably 0.5 mM or more, particularly preferably 1 mM or more. In addition, the upper limit of the phosphorylated Coenzyme is preferably 1 M or less, more preferably 500 mM or less, particularly preferably 200 mM or less. The buffer is not particularly limited, so it may be any of buffers. However, the buffer may be preferably one or a combination of two or more selected from the group consisting of: an oxalic acid buffer, an ethylenediamine tetraacetic acid buffer, a maleic acid buffer, an aspartic acid buffer, a phosphate buffer, an asparagine buffer, a glycine buffer, a pyruvic acid buffer, a pyrophosphate buffer, a malonic acid buffer, a phthalate buffer, a fumaric acid buffer, a tartaric acid buffer, a citrate buffer, a furancarboxylic acid buffer, a β-alanine buffer, a β: β'-dimethyl glutaric acid buffer, a formic acid buffer, a lactic acid buffer, a γ-aminobutyric acid buffer, a barbituric acid buffer, a benzoic acid buffer, a succinic acid buffer, a E-aminocaproic acid buffer, an acetic acid buffer, a propionic acid buffer, a malic acid buffer, a pyridine buffer, a histidine buffer, a cacodylic acid buffer, a carbonic acid buffer, a hydroxyimidazole buffer, a glycerol phosphate buffer, an ethylenediamine buffer, an imidazole buffer, an arsenic acid buffer, a 2,4,6-collidine buffer, a 1-, 2-, or 4-methyl imidazole buffer, an N-ethyl morpholine buffer, a veronal buffer, a barbital buffer, a 2,4-dimethyl imidazole buffer, a morpholine buffer, an N-ethyl morpholine buffer, a 2-amino-2-methyl-1,3-propanediol buffer, a 2-amino-2-ethyl-1,3-propanediol buffer, a diethanolamine buffer, a 4-aminopyridine buffer, a serine buffer, a boric acid buffer, an ammonia buffer, an ethanolamine buffer, an ephedrine buffer, a hydroxyproline buffer, a 2-amino-2-methyl-1-propanol buffer, a leucine buffer, a trimethyl buffer, an α-alanine buffer, a n-propyl alcohol buffer, a methylamine buffer, an ethylamine buffer, a n-butylamine buffer, a triethylamine buffer, a dimethylamine buffer, a hexamethylenediamine buffer, a piperidine buffer, a p-toluenesulfonic acid buffer, a Tris buffer, a glycylglycine buffer, and a GTA buffer; and a Good buffer such as an MES buffer, a Bis-Tris buffer, an ADA buffer, a PIPES buffer, an ACES buffer, an MOPSO buffer, a BES buffer, an MOPS buffer, a TES buffer, an HEPES buffer, a DIPSO buffer, a TAPSO buffer, a POPSO buffer, an HEPPSO buffer, an EPPS buffer, a Tricine buffer, a Bicine buffer, a TAPS buffer, a CHES buffer, a CAPSO buffer, and a CAPS buffer, and preferably selected from the group consisting of a citrate buffer, a diethanolamine buffer, a Tris buffer, a glycine buffer, an acetic acid buffer, a carbonic acid buffer, an imidazole buffer, a 1-, 2-, or 4-methyl imidazole buffer, a veronal buffer, a barbital buffer, a 2,4-dimethyl imidazole buffer, a 2-amino-2-ethyl-1,3-propanediol buffer, a boric acid buffer, a triethylamine buffer, a dimethylamine buffer, and a Good buffer. Optimally, a citrate buffer or a diethanolamine buffer is preferable. The pH of the buffer is preferably from neutral to alkaline when the phosphorylated coenzyme is a reduced type, preferably from pH 7 to 12, optimally pH 7.5 to 11. In addition, when the phosphorylated coenzyme is an acidic type, it is preferably from neutral to acidic, preferably pH 2 to 7.5, optimally pH 3 to 7.

For the stabilization method of the present invention, a preferable method may be one in which a preservative such as sodium azide or proclin is added for improving a general preservation property. A method in which a dried preservation composition is obtained by drying any of those solutions may be also mentioned.

The stabilized composition of the present invention may be one prepared as a composition containing at least a substance for suppressing dephosphorylation reaction of a phosphorylated coenzyme and a phosphorylated coenzyme in accordance with the stabilization method described above. A composition prepared by allowing the composition to further include the above buffer, the above preservative, or the like is also preferable. The composition may be of a liquid or dried form, preferably of a dried form. The dried composition may be prepared by mixing dried products or preferably prepared by preparing a mixture in solution and then drying the mixture. Examples of the drying method include, but not particularly limited to, lyophilization, air-drying, ustulation, and vacuum drying, preferably lyophilization and air-drying, particularly preferably air-drying. The temperature at drying is not particularly limited as far as it is under conditions that do not decompose a phosphorylated coenzyme. It may be −80° C. to 100° C., preferably −50° C. to 80° C., optimally −50° C. to 70° C. Furthermore, the drying time may be suitably defined using the dryness of moisture as an index depending on the drying conditions. The index of the moisture dryness is more preferable as the content of moisture is lower, preferably 10% or less, more preferably 5% or less, optimally 3% or less, extremely preferably 1% or less.

The preservation temperature of the stabilized composition of the present invention is not particularly limited as far as it is defined depending on the purpose. However, the upper limit of the temperature is preferably 50° C. or less, more preferably 40° C. or less, still more preferably 37° C. or less, particularly preferably 32° C. or less, most preferably 30° C. or less. There is no need of specifically defining the lower limit of the temperature. From a practical viewpoint, it is preferably −20° C. or more, more preferably −10° C. or more, still more preferably 0° C. or more, particularly preferably 4° C. or more, most preferably 10° C. or more. The characteristic feature of the stabilization method of the present invention is that a stable preservation can be attained at temperatures ranging from −20° C. to 40° C., from 4° C. to 37° C., or from 10° C. and 32° C.

In this way, by the use of a coenzyme that can be preserved at normal temperature for a prolonged period, it becomes possible to provide a high-sensitive assay for ALP activity, which can be also retained at room temperature for a prolonged period, for the first time. In the assay for ALP activity, for example, NADP being preserved in dried state is redissolved in a reaction solution containing 12α hydroxysteroid dehydrogenase, diaphorase, cholic acid, nitroblue-tetrazolium dissolved in a buffer and ALP to be measured is then added to the reaction solution, followed by incubating at room temperature or 37° C. for a predetermined period. The amount of pigments accumulated in the solution may be determined as an increment per unit time or an accumulated absolute amount by a spectrophotometer or visual observation. For the usage of such an assay for ALP activity, as described above, it can be commonly used for a detection reagent, a detection kit containing such a detection reagent, and so on in any fields of examination. An example thereof includes a reagent for detecting $E.$ $coli$ O-157, which can be preserved at room temperature. Furthermore, the kit may be one composed of a plate on which an O-157 gene probe is immobilized, a sample extract, a digoxigenin-labeled nucleic acid, an anti-digoxigenin ALP-labeled antibody, a washing solution, an NADP-dried product for ALP detection, an enzyme-dried product for ALP detection, and an ALP detection reagent-dissolving solution, which can be preserved as a reagent at room temperature.

For describing the method simply, an O-157 gene-immobilized plate is prepared by immobilizing a probe nucleic acid for detecting an $E.$ $coli$ O-157 gene on a plastic plate. A sample extract obtained from the nucleic acid of $E.$ $coli$ O-157 as a sample is dispensed into the plate, and then incubated at room temperature or 37° C. for a predetermined period. The plate is washed with a washing solution and then added with a digoxigenin-labeled nucleic acid, which has a sequence complement to that of the $E.$ $coli$ O-157 gene and has a region different from that of the probe on the plate solid phase, followed by incubation at room temperature or 37° C. for a predetermined period. The plate is washed and then added with an anti-digoxigenin ALP-labeled antibody, followed by incubation at room temperature or 37° C. for a predetermined period. After washing to the plate, for detecting an anti-digoxigenin ALP-labeled antibody-digoxigenin-nucleic acid complex formed on the solid phase, an enzyme-dried product for ALP detection containing 12α hydroxysteroid dehydrogenase, diaphorase, cholic acid, and nitroblue tetrazolium and a reaction solution for ALP detection prepared by re-dissolving an NADP-dried product for ALP detection in an ALP detection reagent-dissolving solution were added to the plate in certain amounts, followed by incubation at room temperature or 37° C. for a predetermined period. The presence of $E.$ $coli$ O-157 in the sample is confirmed by reading out using an optical device such as a plate reader or visually determining the amount of a color-developed formazan pigment on the plate. If $E.$ $coli$ O-157 is present, the ALP activity supported by the O-157 gene shows a strong color development. In contrast, if $E.$ $coli$ O-157 is absent, the color development does not occur or is extremely small.

Furthermore, the use of a substance for suppressing dephosphorylation reaction for stabilizing the phosphorylated enzyme for a prolonged period, the use of polysaccharides containing glucose as a constituent for preventing the dephosphorylation reaction of at least a phosphorylated coenzyme, and a method of preserving a phosphorylated coenzyme for a prolonged period using at least a substance for suppressing dephosphorylation reaction of the phosphorylated coenzyme are also within the scope of the present invention.

The coenzyme of the present invention stabilized as described above can be applied to a simplified immunoassay device using an enzyme cycling method, so the simplified immunoassay device can be also within the scope of the present invention. The principle of the simplified immunoassay device is preferably an immunochromatographic method or a flow-through method with the flow-through method being preferable. The simplified immunoassay device may be of, for example, in the case of the flow-through method, immobilizing an antibody or the like having a binding ability to a substance to be provided as a measurement object in advance on a membrane; mounting such a membrane on a material having water-absorption ability; and, for allowing the membrane to capture the measurement object, carrying out an antigen-antibody reaction by dropping onto the membrane a liquid in which the measurement object is previously reacted with another enzyme-labeled antibody having the binding ability to the measurement object, or dropping a liquid containing the measurement object and dropping an enzyme-labeled antibody solution after the liquid is substantially depleted from the membrane by absorption of the liquid. Subsequently, after the liquid is substantially depleted from the membrane, a washing solution is dropped as a washing operation, and similarly after the washing solution is depleted from the membrane, an enzyme substrate solution is added. In general, the enzyme in the complex formed on the membrane is reacted with the enzyme substrate to confirm the formation of a pigment on the membrane.

In this case, for efficiently forming a complex containing the enzyme-labeled antibody on the membrane, the duration of contacting the enzyme-labeled antibody solution with the membrane is longer the better. In contrast, in view of operability, the washing solution and the enzyme substrate solution may preferably permeate through the membrane within a shorter period. Therefore, it is a common method in which the substance provided as a measurement object and the enzyme-labeled antibody may be added with a predetermined time interval, and the washing solution, the enzyme substrate solution, and so on are added with a shorter interval in that order. This method has a problem in the viewpoint of operability.

In the present invention, as a method of improving a plurality of operations with such time intervals, a plurality of liquids is added to a simplified immunoassay device substantially at the same time and the liquids are then added to a membrane in order by an automatic solution-sending device incorporated in the inside of the device. In particular, when an enzyme-labeled antibody and an enzyme substrate solution are mixed on the membrane, a color development may occur without depending on the presence or absence of a substance provided as a measurement object, thereby causing a nonspecific background. Therefore, for avoiding such a trouble, the inventors of the present invention have invented a simplified immunoassay device in which an automatic solution-sending device for preventing them from contacting with each other, as much as possible. The automatic solution-sending device provides a time lag so that, when both an enzyme-labeled antibody solution and an enzyme substrate solution is charged into the device simultaneously, first the enzyme-labeled antibody solution permeates through the membrane for, a predetermined period, and the enzyme substrate solution is then added after the permeation through the membrane is substantially completed. When the time lag is provided, anything can be used. For example, there is a method in which, when the enzyme substrate solution is added, the solution may be blocked by an water-soluble filter before the liquid approaches to the membrane and then the enzyme substrate solution is added to the membrane after a predetermined time period during which the water-soluble filter can be dissolved.

The water-soluble filter allows an enzyme substrate solution not to flow out for a predetermined period and allows it to flow out after the water-soluble filter is dissolved by the enzyme substrate solution at a certain point of time. Therefore, any filter can be used as far as it does not substantially influence an enzyme reaction. For example, a film-shaped filter having water-soluble property is preferable.

Examples of the film-shaped filter having water-soluble property include a polyvinyl alcohol membrane, a pullulan membrane, and a hydroxypropyl cellulose membrane. Among them, preferable is the polyvinyl alcohol membrane. Any of these water-soluble filters is mounted on the lower part of a cylindrical enzyme substrate solution adding vessel. When the enzyme substrate solution is added, the solution does not flow out for a predetermined time while dissolving the water-soluble filter, and after that, the solution begins to flow. The time period that does not allow the solution to flow is in the range of 10 seconds to 10 minutes, preferably 30 seconds to 5 minutes.

Furthermore, for the automatic solution-sending device of the present invention, a method using a siphon may be employed. The siphon of the present invention is a tube having an opening at the lower part of an enzyme substrate solution adding vessel, where the tube has a structure that extends from the opening to the upper part and then extends to the lower part, while the other opening of the tube is located at a portion communicating with an observation window. Besides, the siphon may be provided with a filter for controlling the flow rate of the enzyme substrate solution, which is located between the lower part and the upper end of the enzyme substrate solution adding vessel. When an enzyme substrate solution is added to the enzyme substrate solution adding vessel having a siphon structure, the solution is gradually accumulated in the lower part of the enzyme substrate solution adding vessel by a flow-rate control filter. Subsequently, the tube is filled with the solution so as to correspond to the height of the liquid in accordance with an increase in preservation. When the surface of the preserved solution becomes higher than the highest position of the tube, the preserved solution passes through the tube and flows into an observation window at once. Therefore, when the enzyme substrate solution is added to the enzyme substrate solution adding vessel, the solution does not flow for a given period of time and then flows out at once. Any of flow-rate control filters can be used as far as an enzyme substrate solution is allowed to moderately flow out to the lower part of an enzyme substrate solution adding vessel after the enzyme substrate solution is added to the enzyme substrate solution adding vessel and a filter paper on which a water-soluble substance is dried is preferable. The material of such filter paper may be any substance as far as it allows the permeation of a solution after re-dissolving the water-soluble substance. For examples, the materials include paper, glass, polyester, polystyrene, and nylon. Among them, paper or glass is preferable. The water-soluble substances include sugars, proteins, and synthetic polymers. The sugars include macromolecular polysaccharides such as dextran, pullulan, and agar; dissacharides such as sucrose, lactose, and maltose; and monosaccharides such as glucose and galactose. Among them, the macromolecular polysaccharides are preferable and dextran is more preferable. The proteins include albumin and globulin. The synthetic polymers include polyethylene glycol, polyvinylpyrrolidone, polyvinyl alcohol, and hydroxypropylcellulose. The flow rate of the solution may be suitably adjusted by the concentration of the water-soluble substance in the dry state, and the time period that does not allow the solution to flow is 10 seconds to 10 minutes, preferably 30 seconds to 5 minutes.

By using those, it is also easy to add a washing solution by a similar way before the addition of the enzyme substrate solution to the observation window. However, such an addition is not always required. The addition may be set depending on the background which can be recognized in the absence of a substance to be measured and the required sensitivity. For operability and cost effectiveness, it is preferable not to use the washing solution.

For more detailed description, for example, an influenza antigen suspension is obtained by collecting a liquid wiped out from a nasal cavity of a patient infected with influenza by using a swab or the like, and suspending an influenza antigen attached to the swab in a solution of an alkaline phosphatase-labeled anti-influenza antibody, which contains a surfactant, which serves as an influenza antigen extract, an appropriate buffer, salts, and so on.

An appropriate amount of the influenza antigen suspension is dropped to the observation window of the simplified immunoassay device and an enzyme-cycling reaction solution is immediately added to the enzyme substrate solution adding vessel. After several minutes, the presence or absence of antigen may be visually confirmed by observation of pigment precipitation through the observation window, so the presence or absence of antigen can be determined without any specific operation after the addition of the influenza antigen suspension and the enzyme-cycling reaction solution.

Furthermore, for detecting other microorganisms other than influenza, it is also possible to provide a simplified immunoassay having excellent specificity and detection sensitivity by making a combination of an antibody against a microbial ribosomal protein and an enzyme cycling method as described in WO 00/06603. The ribosomal protein used may be L7/L12. In particular, the simplified immunoassay is effective to *Mycoplasma pneumoniae, Hemophilus influenza, Streptococcus pneumoniae, Chlamydia pneumoniae, Chlamydia trachomatis,* and *Legionella pneumophila,* on which excellent specificity and binding ability are demanded. *Mycoplasma pneumoniae* or *Legionella pneumophila* is preferable, and preferably it is desirable to use an antibody against *Mycoplasma pneumoniae.*

EXAMPLES

Hereinafter, the present invention is further described with reference to examples and comparative examples. However, the present invention is not restricted by these examples.

Example 1

(1) Preservation of Coenzyme

In a 20 mM sodium citrate buffer (pH 6.5) containing 5% lactose, NADP (manufactured by Oriental Yeast Co., Ltd.) as a coenzyme was dissolved to be 1.25 mM to prepare a solution. In addition, as a control, a solution was prepared by dissolving NADP in a 20 mM sodium citrate buffer (pH 6.5) so as to be 1.25 mM, and five different solutions in total were prepared. The solutions were each dispensed into microtubes at an amount of 20 per microtube and dried for 5 hours under the conditions at 30° C. with 15% humidity. After drying, the microtubes were preserved at 4° C., 25° C., 32° C., 37° C., and 42° C., respectively, in an aluminum bag containing a desiccant.

(2) Measurement of Background

As an enzyme-cycling reaction solution, a solution containing 100 mM diethanolamine-HCl (pH 9.5), 0.0125% nitroblue tetrazolium, 1 mM cholic acid, 50 mM sodium chloride, 1 mM magnesium chloride, and 6.6 U/ml diaphorase from *Bacillus megaterium* (manufactured by Asahikasei Pharma Corporation) was prepared. One milliliter of the solution was added to a microtube in which NADP bad been preserved in the dry state and the NADP was then stirred and redissolved therein. In a tube, 500 µl of the cycling reaction solution containing the redissolved NADP was heated at 37° C. for 3 minutes and then added with 5 µl of 1777.6 U/ml 12α hydroxysteroid dehydrogenase (manufactured by Asahikasei Pharma Corporation) from *Bacillus sphaericus* dissolved in 10 mM PIPES (pH 8.5), followed by reacting at 37° C. for 5 minutes. The reaction was terminated by the addition of 250 µl of a 0.5% sodium dodecylsulfate solution and the reaction solution was then subjected to the measurement of absorbance at 550 nm.

(3) Measurement of Alkaline Phosphatase Activity

In a tube, 500 µl of the cycling reaction solution containing the redissolved NADP obtained in the above-mentioned item (2) was heated at 37° C. for 3 minutes, then simultaneously added with 5 µl of 1777.6 U/ml 12α hydroxysteroid dehydrogenase (manufactured by Asahikasei Pharma Corporation) from *Bacillus sphaericus* dissolved in 10 mM PIPES (pH 8.5) and 5 µl of 50 mU/ml of alkaline phosphatase from calf small intestine (manufactured by Roche Co., Ltd.) and then reacted at 37° C. for 5 minutes. The reaction was terminated by the addition of 250 µl of a 0.5% sodium dodecylsulfate solution and the reaction solution was then subjected to the measurement of absorbance at 550 nm. The values of background obtained in the above-mentioned item (2) under the respective experimental conditions were subtracted from the resulting measurement values and the obtained values were then provided as activity values obtained by the alkaline phosphatase reaction, respectively.

(4) Measurement of NADP Amount

NADP preserved in the dry state was re-dissolved by the addition of 1 ml of a 10-mM PIPES (pH 8) and a part thereof was then diluted 10-fold into distilled water. In 1 ml of a solution which was prepared such that the enzyme-cycling reaction solution prepared in the above-mentioned item (2) contained 8 U/ml alkaline phosphatase from calf small intestine, was added with 20 µl of a previously-prepared NADP-redissolved solution, followed by reacting at 37° C. for 5 minutes. The reaction was terminated by the addition of 250 µl of a 0.5% sodium dodecylsulfate solution and the reaction solution was then subjected to the measurement of absorbance at 550 nm. The measurement value of NADP at the start of preservation was defined as 100% and the remaining % was then calculated.

As a result, as shown in Table 1-1 and Table 1-2, the addition of lactose attained a decrease in background after 3-month preservation as compared with the experimental control and the ALP activity was also measured. In addition, as shown in Table 1-3, the amount of NADP remained was also retained as compared with the experimental control.

TABLE 1-1

| Background | Immediately after the | 3-month preservation | | | | |
|---|---|---|---|---|---|---|
| Abs: 550 nm | start of preservation | 4° C. | 25° C. | 32° C. | 37° C. | 42° C. |
| 5% lactose | 0.067 | 0.071 | 0.081 | 0.122 | 0.224 | 0.259 |
| Experimental control | 0.067 | 0.183 | 0.386 | 0.608 | 1.233 | 1.956 |

TABLE 1-2

| Measurement value of ALP activity Abs: 550 nm | Immediately after the start of preservation | 3-month preservation | | | | |
|---|---|---|---|---|---|---|
| | | 4° C. | 25° C. | 32° C. | 37° C. | 42° C. |
| 5% lactose | 0.276 | 0.274 | 0.288 | 0.262 | 0.239 | 0.200 |
| Experimental control | 0-278 | 0.287 | 0.283 | 0.305 | 0.210 | 0.129 |

TABLE 1-3

| Remaining % of NADP amount | Immediately after the start of preservation | 3-month preservation | | | | |
|---|---|---|---|---|---|---|
| | | 4° C. | 25° C. | 32° C. | 37° C. | 42° C. |
| 5% lactose | 100 | 99 | 100 | 100 | 91 | 63 |
| Experimental control | 100 | 91 | 88 | 76 | 43 | 31 |

Example 2

An experiment was conducted in a manner similar to Example 1 except that three different solutions were prepared by dissolving NADP (manufactured by Oriental Yeast Co., Ltd.) as a coenzyme so as to be 1.25 mM in 20-mM sodium citrate buffers (pH 6.5) that contained, instead of 5% lactose, 10% trehalose, 10% maltose, and 10% sucrose, respectively.

As a result, as shown in Table 2-1 to Table 2-3, each of the conditions of 10% trehalose, 10% maltose, and 10% sucrose showed good stability as compared with the experimental control.

Example 3

An experiment was conducted in a manner similar to Example 1 except that six different solutions were prepared by dissolving NADP (manufactured by Oriental Yeast Co., Ltd.) as a coenzyme so as to be 1.25 mM in 20-mM sodium citrate buffers (pH 6.5) that contained, instead of 5% lactose, trehalose adjusted to concentrations of 0.1%, 1%, 5%, 10%, 30%, and 60%, respectively.

As a result, as shown in Table 3-1 to Table 3-3, in the range of 0.1% to 60% trehalose concentrations, good stability was obtained as compared with the experimental control.

TABLE 2-1

| Background Abs: 550 nm | Immediately after the start of preservation | 3-month preservation | | | | |
|---|---|---|---|---|---|---|
| | | 4° C. | 25° C. | 32° C. | 37° C. | 42° C. |
| 10% trehalose | 0.067 | 0.066 | 0.101 | 0.139 | 0.588 | 0.772 |
| 10% maltose | 0.094 | 0.093 | 0.109 | 0.146 | 0.225 | 0.292 |
| 10% sucrose | 0.067 | 0.068 | 0.108 | 0.164 | 0.622 | 0.783 |
| Experimental control | 0.067 | 0.183 | 0.386 | 0.608 | 1.233 | 1.956 |

TABLE 2-2

| Measurement value of ALP activity Abs: 550 nm | Immediately after the start of preservation | 3-month preservation | | | | |
|---|---|---|---|---|---|---|
| | | 4° C. | 25° C. | 32° C. | 37° C. | 42° C. |
| 10% trehalose | 0.276 | 0.261 | 0.271 | 0.263 | 0.195 | 0.128 |
| 10% maltose | 0.299 | 0.302 | 0.287 | 0.278 | 0.240 | 0.199 |
| 10% sucrose | 0.276 | 0.291 | 0.275 | 0.269 | 0.188 | 0.138 |
| Experimental control | 0.278 | 0.287 | 0.283 | 0.305 | 0.210 | 0.129 |

TABLE 2-3

| Remaining % of NADP amount | Immediately after the start of preservation | 3-month preservation | | | | |
|---|---|---|---|---|---|---|
| | | 4° C. | 25° C. | 32° C. | 37° C. | 42° C. |
| 10% trehalose | 100 | 96 | 105 | 97 | 75 | 60 |
| 10% maltose | 100 | 97 | 102 | 97 | 74 | 68 |
| 10% sucrose | 100 | 97 | 89 | 72 | 67 | 46 |
| Experimental control | 100 | 91 | 88 | 76 | 43 | 31 |

TABLE 3-1

| Background Abs: 550 nm | Immediately after the start of preservation | 3-month preservation ||||| 
|---|---|---|---|---|---|---|
| | | 4° C. | 25° C. | 32° C. | 37° C. | 42° C. |
| 0.1% trehalose | 0.068 | 0.130 | 0.202 | 0.323 | 0.888 | 1.237 |
| 1% trehalose | 0.067 | 0.089 | 0.124 | 0.191 | 0.765 | 0.980 |
| 5% trehalose | 0.066 | 0.071 | 0.109 | 0.160 | 0.633 | 0.800 |
| 10% trehalose | 0.067 | 0.066 | 0.101 | 0.139 | 0.588 | 0.772 |
| 30% trehalose | 0.065 | 0.058 | 0.098 | 0.152 | 0.497 | 0.702 |
| 60% trehalose | 0.064 | 0.055 | 0.111 | 0.143 | 0.488 | 0.695 |
| Experimental control | 0.067 | 0.183 | 0.386 | 0.608 | 1.233 | 1.956 |

TABLE 3-2

| Measurement value of ALP activity Abs: 550 nm | Immediately after the start of preservation | 3-month preservation |||||
|---|---|---|---|---|---|---|
| | | 4° C. | 25° C. | 32° C. | 37° C. | 42° C. |
| 0.1% trehalose | 0.275 | 0.276 | 0.288 | 0.299 | 0.200 | 0.121 |
| 1% trehalose | 0.266 | 0.262 | 0.275 | 0.271 | 0.188 | 0.132 |
| 5% trehalose | 0.265 | 0.270 | 0.272 | 0.261 | 0.202 | 0.123 |
| 10% trehalose | 0.276 | 0.261 | 0.271 | 0.263 | 0.195 | 0.128 |
| 30% trehalose | 0.280 | 0.277 | 0.289 | 0.274 | 0.223 | 0.188 |
| 60% trehalose | 0.271 | 0.269 | 0.276 | 0.280 | 0.230 | 0.174 |
| Experimental control | 0.278 | 0.287 | 0.283 | 0.305 | 0.210 | 0.129 |

TABLE 3-3

| Remaining % of NADP amount | Immediately after the start of preservation | 3-month preservation |||||
|---|---|---|---|---|---|---|
| | | 4° C. | 25° C. | 32° C. | 37° C. | 42° C. |
| 0.1% trehalose | 100 | 102 | 102 | 83 | 66 | 40 |
| 1% trehalose | 100 | 100 | 103 | 89 | 69 | 58 |
| 5% trehalose | 100 | 99 | 95 | 101 | 69 | 57 |
| 10% trehalose | 100 | 96 | 105 | 97 | 75 | 60 |
| 30% trehalose | 100 | 101 | 100 | 98 | 81 | 64 |
| 60% trehalose | 100 | 96 | 99 | 98 | 79 | 66 |
| Experimental control | 100 | 91 | 88 | 76 | 43 | 31 |

Example 4

An experiment was conducted in a manner similar to Example 1 except that five different solutions were prepared by dissolving NADP (manufactured by Oriental Yeast Co., Ltd.) as a coenzyme so as to be 1.25 mM in 20-mM sodium citrate buffers (pH 6.5) that contained, instead of 5% lactose, lactose adjusted to concentrations of 0.1%, 0.5%, 1%, 5%, and 15%, respectively.

As a result, as shown in Table 4-1 to Table 4-3, in the range of 0.1% to 15% lactose concentrations, good stability was obtained as compared with the experimental control.

TABLE 4-1

| Background Abs: 550 nm | Immediately after the start of preservation | 3-month preservation |||||
|---|---|---|---|---|---|---|
| | | 4° C. | 25° C. | 32° C. | 37° C. | 42° C. |
| 0.1% lactose | 0.069 | 0.090 | 0.142 | 0.233 | 0.488 | 0.605 |
| 0.5% lactose | 0.066 | 0.083 | 0.112 | 0.153 | 0.312 | 0.386 |
| 1% lactose | 0.065 | 0.070 | 0.071 | 0.131 | 0.253 | 0.297 |
| 5% lactose | 0.067 | 0.071 | 0.081 | 0.122 | 0.224 | 0.259 |
| 15% lactose | 0.071 | 0.065 | 0.066 | 0.111 | 0.196 | 0.240 |
| Experimental control | 0.067 | 0.183 | 0.386 | 0.608 | 1.233 | 1.956 |

TABLE 4-2

| Measurement value of ALP activity Abs: 550 nm | Immediately after the start of preservation | 3-month preservation | | | | |
|---|---|---|---|---|---|---|
| | | 4° C. | 25° C. | 32° C. | 37° C. | 42° C. |
| 0.1% lactose | 0.278 | 0.278 | 0.283 | 0.267 | 0.206 | 0.130 |
| 0.5% lactose | 0.295 | 0.292 | 0.276 | 0.231 | 0.237 | 0.143 |
| 1% lactose | 0.276 | 0.266 | 0.281 | 0.253 | 0.254 | 0.188 |
| 5% lactose | 0.276 | 0.274 | 0.288 | 0.262 | 0.239 | 0.200 |
| 15% lactose | 0.280 | 0.291 | 0.290 | 0.263 | 0.241 | 0.213 |
| Experimental control | 0.278 | 0.287 | 0.283 | 0.305 | 0.210 | 0.129 |

TABLE 4-3

| Remaining % of NADP amount | Immediately after the start of preservation | 3-month preservation | | | | |
|---|---|---|---|---|---|---|
| | | 4° C. | 25° C. | 32° C. | 37° C. | 42° C. |
| 0.1% lactose | 100 | 95 | 95 | 95 | 77 | 33 |
| 0.5% lactose | 100 | 96 | 95 | 93 | 88 | 45 |
| 1% lactose | 100 | 98 | 103 | 99 | 92 | 58 |
| 5% lactose | 100 | 99 | 100 | 100 | 91 | 63 |
| 15% lactose | 100 | 101 | 100 | 96 | 97 | 71 |
| Experimental control | 100 | 91 | 88 | 76 | 43 | 31 |

Example 5

An experiment was conducted in a manner similar to Example 1 except that four different solutions were prepared by dissolving NADP (manufactured by Oriental Yeast Co., Ltd.) as a coenzyme so as to be 1.25 mM in 20-mM sodium citrate buffers (pH 6.5) that contained, instead of 5% lactose: condition 1 with 10% lactose and 20% trehalose; condition 2 with 10% lactose and 20% maltose; condition 3 with 20% trehalose and 20% maltose; and condition 4 with 10% lactose, 20% trehalose, and 20% maltose, respectively.

As a result, as shown in Table 5-1 to Table 5-3, each of the conditions 1 to 4 showed good stability as compared with the experimental control.

TABLE 5-1

| Background Abs: 550 nm | Immediately after the start of preservation | 3-month preservation | | | | |
|---|---|---|---|---|---|---|
| | | 4° C. | 25° C. | 32° C. | 37° C. | 42° C. |
| Condition 1 | 0.065 | 0.070 | 0.088 | 0.124 | 0.244 | 0.287 |
| Condition 2 | 0.071 | 0.081 | 0.080 | 0.113 | 0.192 | 0.229 |
| Condition 3 | 0.084 | 0.079 | 0.090 | 0.126 | 0.225 | 0.255 |
| Condition 4 | 0.066 | 0.072 | 0.084 | 0.112 | 0.180 | 0.203 |
| Experimental control | 0.067 | 0.183 | 0.386 | 0.608 | 1.233 | 1.956 |

TABLE 5-2

| Measurement value of ALP activity Abs: 550 nm | Immediately after the start of preservation | 3-month preservation | | | | |
|---|---|---|---|---|---|---|
| | | 4° C. | 25° C. | 32° C. | 37° C. | 42° C. |
| Condition 1 | 0.288 | 0.291 | 0.287 | 0.280 | 0.229 | 0.140 |
| Condition 2 | 0.264 | 0.277 | 0.280 | 0.285 | 0.232 | 0.151 |
| Condition 3 | 0.277 | 0.266 | 0.265 | 0.274 | 0.227 | 0.136 |
| Condition 4 | 0.271 | 0.288 | 0.275 | 0.289 | 0.265 | 0.189 |
| Experimental control | 0.278 | 0.287 | 0.283 | 0.305 | 0.210 | 0.129 |

TABLE 5-3

| Remaining % of NADP amount | Immediately after the start of preservation | 3-month preservation | | | |
|---|---|---|---|---|---|
| | | 4° C. | 25° C. | 32° C. | 37° C. | 42° C. |
| Condition 1 | 100 | 99 | 101 | 92 | 84 | 45 |
| Condition 2 | 100 | 98 | 98 | 95 | 86 | 50 |
| Condition 3 | 100 | 99 | 100 | 97 | 88 | 45 |
| Condition 4 | 100 | 100 | 101 | 101 | 90 | 59 |
| Experimental control | 100 | 91 | 88 | 76 | 43 | 31 |

Example 6

Two different solutions were prepared by dissolving NADP (manufactured by Oriental Yeast Co., Ltd.) as a coenzyme so as to be 1.25 mM in 20-mM sodium citrate buffers (pH 6.5) that contained 5% lactose described in Example 1 and 10 trehalose described in Example 2, respectively. The solutions were each dispensed into microtubes at an amount of 20 μl per tube and dried for 5 hours under the conditions at 30° C. with 15% humidity. After drying, the microtubes were preserved for 6 months at 4° C., 25° C., and 35° C. in an aluminum bag containing a desiccant and then their backgrounds, ALP activities, and NADP-remaining amounts were determined, respectively.

As a result, as shown in Table 6-1 to Table 6-3, both 5% lactose and 10% trehalose showed good stabilities under any of conditions as compared with the experimental control.

TABLE 6-1

| Background Abs: 550 nm | Immediately after the start of preservation | 6-month preservation | | |
|---|---|---|---|---|
| | | 4° C. | 25° C. | 32° C. |
| 5% lactose | 0.067 | 0.079 | 0.097 | 0.141 |
| 10% trehalose | 0.067 | 0.068 | 0.111 | 0.158 |
| Experimental control | 0.067 | 0.183 | 0.386 | 0.608 |

TABLE 6-2

| Measurement value of ALP activity Abs: 550 nm | Immediately after the start of preservation | 6-month preservation | | |
|---|---|---|---|---|
| | | 4° C. | 25° C. | 32° C. |
| 5% lactose | 0.276 | 0.303 | 0.281 | 0.257 |
| 10% trehalose | 0.276 | 0.298 | 0.257 | 0.248 |
| Experimental control | 0.278 | 0.238 | 0.262 | 0.292 |

TABLE 6-3

| Remaining % of NADP amount | Immediately after the start of preservation | 6-month preservation | | |
|---|---|---|---|---|
| | | 4° C. | 25° C. | 32° C. |
| 5% lactose | 100 | 102 | 91 | 77 |
| 10% trehalose | 100 | 105 | 95 | 95 |
| Experimental control | 100 | 99 | 92 | 65 |

Example 7

For one of two different anti-A influenza virus monoclonal antibodies (manufactured by Fitzgerald Co., Ltd.), 1 μl of an antibody solution (2 mg/ml) was spotted on a nitrocellulose membrane (manufactured by Whatman Co., Ltd.) of 25 mm×30 mm and then dried at 42° C. for 30 minutes. The dried nitrocellulose membrane was then mounted on a water-absorbing pad. Subsequently, a top cover was closed so that a previously-opened observation window in the cover corresponded to the spotted portion. A water-soluble filter KC40 (manufactured by Aicello chemical Co., Ltd.) made of polyvinyl alcohol as shown in FIG. 1 was attached on the lower part of a enzyme substrate solution adding vessel and an enzyme substrate filling port was formed in the opening of a top cover of a simplified immunoassay device, thereby completing a simplified immunoassay device.

The other kind of the anti-A influenza virus monoclonal antibody in amount of 0.15 mg was labeled with a commercially available alkaline phosphatase labeling kit, thereby obtaining the labeled anti-A influenza virus monoclonal antibody. This labeled antibody was diluted 4,000-fold into a Tris-HCl buffer (pH 7.5) containing 2% BSA to prepare an enzyme-labeled antibody dilution.

A simulated sample was obtained by diluting 0.75 mg/ml of A-type influenza virus antigen H3N2 (manufactured by HyTest Co., Ltd.) so as to be 0.1 μg/ml with PBS containing 0.2% BSA and 0.1% Triton X-100 and soaking 50 μl of the dilution into a swab. An experimental control used was a swab soaked with 50 μl of a dilute solution.

The swab well-soaked with the influenza antigen was placed in 0.2 ml of the enzyme-labeled antigen dilution, and the dilution was then sufficiently stirred, followed by adding the total amount thereof to the previously-formed observation window of the simple immunoassay device. Promptly without any interval, 500 μl of the enzyme-cycling reaction solution of Example 1 was added to the enzyme substrate solution adding vessel. After 10 minutes from the addition, the presence or absence of a blue pigment on the nitrocellulose membrane was visually observed.

Results

| | Visual observation |
|---|---|
| H3N2 antigen added | + |
| Experimental control | − |

As described above, it was judged positive only when the influenza antigen was added, so a simple test using the simplified immunoassay device shown in FIG. 1 was able to be demonstrated.

Example 8

According to Example 6, the anti-A influenza virus monoclonal antibody was immobilized on a nitrocellulose membrane and covered with a top cover. As a enzyme substrate solution adding vessel, a simplified immunoassay device was formed such that a filter, which was soaked with a 40% sucrose solution and then dried, was attached on the upstream portion of a siphon structure shown in FIG. 2 and an enzyme substrate filling port was formed in the opening of the top cover of the simplified immunoassay device. The subsequent procedures were carried out in a manner similar to Example 6. The presence or absence of a blue pigment on the nitrocellulose membrane was visually observed.

Results

|  | Visual observation |
|---|---|
| H3N2 antigen added | + |
| Experimental control | − |

Figure 2:
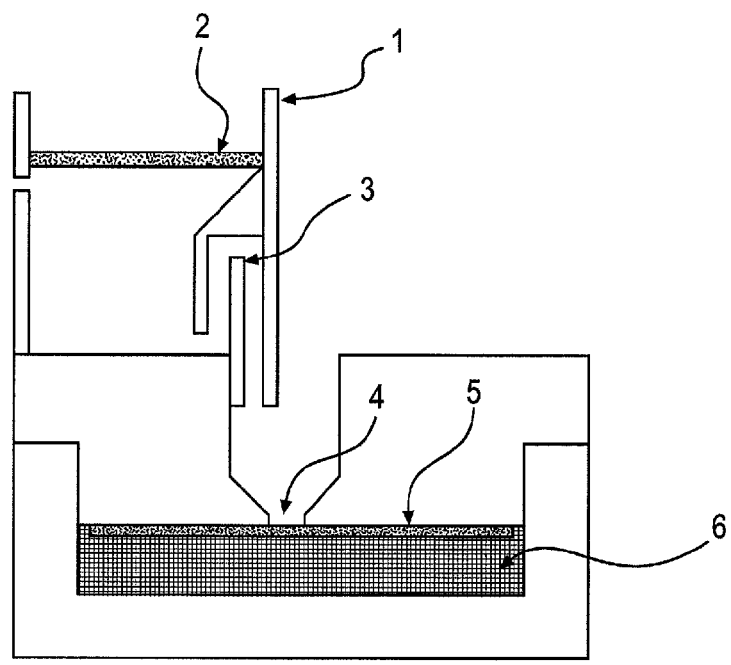
FIG. 2 is a drawing showing a flow-through simplified immunoassay device of the present invention, which is provided with a siphon-type solution-sending device so that an enzyme substrate is automatically added after allowing an enzyme-labeled reagent to permeate through an antibody- or antigen-immobilized membrane.

As described above, it was judged positive only when the influenza antigen was added, so a simple test using the simplified immunoassay device shown in FIG. 2 was able to be demonstrated.

INDUSTRIAL APPLICABILITY

The present invention provides a stabilization method for a phosphorylated coenzyme particularly at around room temperature, which can be preferably used in the fields of clinical diagnosis, food evaluation, an examination for biogenic substances, and so on.

The invention claimed is:

1. A stabilization method for a phosphorylated coenzyme, comprising allowing at least a substance for suppressing dephosphorylation reaction of a phosphorylated coenzyme to coexist with a phosphorylated coenzyme.

2. A stabilization method for a phosphorylated coenzyme in a dry state, comprising: allowing at least a substance for suppressing dephosphorylation reaction of a phosphorylated coenzyme to coexist with a phosphorylated coenzyme in a solution; and drying the solution.

3. The stabilization method according to claim 1, wherein the substance for suppressing dephosphorylation reaction is a sugar and/or a sugar alcohol.

4. The stabilization method according to claim 1, wherein the substance for suppressing dephosphorylation reaction is a polysaccharide containing glucose as a constituent.

5. The stabilization method according to claim 4, wherein the substance for suppressing dephosphorylation reaction is a disaccharide containing glucose as a constituent.

6. The stabilization method according to claim 5, wherein the substance for suppressing dephosphorylation reaction is one or a combination of two or more selected from the group consisting of lactose, trehalose, maltose, and sucrose.

7. The stabilization method according to claim 2, wherein the drying is performed by air-drying.

8. The stabilization method according to claim 1, wherein the phosphorylated coenzyme is nicotinamide adenine dinucleotide phosphate (NADP).

9. The method according to claim 1, wherein stabilization occurs for a prolonged period.

10. A method for stabilizing a phosphorylated coenzyme, comprising allowing trehalose and at least one of lactose, maltose, and sucrose to coexist with the phosphorylated coenzyme.

11. The method according to claim 10, comprising allowing trehalose and at least one of lactose, maltose, and sucrose to coexist with a phosphorylated coenzyme in a solution; and further comprising drying the solution.

* * * * *